United States Patent [19]

Rubin

[11] Patent Number: 4,568,640

[45] Date of Patent: Feb. 4, 1986

[54] METHOD OF INSERTING AMINO ACID ANALOGS INTO PROTEINS

[76] Inventor: Harvey Rubin, 2560 First Ave., San Diego, Calif. 92103

[21] Appl. No.: 476,925

[22] Filed: Mar. 21, 1983

Related U.S. Application Data

[63] Continuation-in-part of Ser. No. 262,303, May 11, 1981, abandoned.

[51] Int. Cl.$^4$ ............................................. C12P 21/02
[52] U.S. Cl. .................................. 435/70; 260/112 R; 260/112.5 R; 435/68; 935/3; 935/20; 935/111
[58] Field of Search ..................... 435/68, 69, 70, 71, 435/91, 92; 260/112 R, 112.5 R; 935/3, 111, 20

[56] References Cited

U.S. PATENT DOCUMENTS

| 4,351,901 | 9/1982 | Bahl | 435/68 X |
| 4,469,631 | 9/1984 | Baxter | 435/68 X |

OTHER PUBLICATIONS

Jelenc, P. C. et al., Proc. Natl. Acad. Sci. USA, 76(7), 3174–3178, (Jul. 1979).

*Primary Examiner*—Sidney Marantz
*Attorney, Agent, or Firm*—Frank D. Gilliam

[57] ABSTRACT

A method for substituting one amino acid for another in a protein chain to improve selected properties of the protein. Initially, an mRNA molecule capable of producing an unmodified protein of the type it is desired to modify is provided. Next the codon along the mRNA chain which ordinarily accepts the anti-codon corresponding to a first amino acid which is to be replaced with a selected second amino acid is determined. The tRNA which ordinarily brings the first amino acid to that site is modified to carry the second amino acid instead. The modified protein is then formed by translation techniques in the presence of the modified tRNA, whereby the second amino acid is incorporated in the protein chain in place of the first amino acid. Several methods of accomplishing the modification of the selected tRNA are also disclosed.

7 Claims, No Drawings

METHOD OF INSERTING AMINO ACID ANALOGS INTO PROTEINS

BACKGROUND OF THE INVENTION

This application is a Continuation-in-Part of Application Ser. No. 262,303 filed May 11, 1981 and now abandoned.

For some time it has been known that DNA (deoxyribonucleic acid) molecules contain the instructions for the assembly and organization of living systems. The nucleotide bases along the DNA molecule chain, arranged in specific sequences sometimes referred to as "genetic codes", specify the structure of the thousands of proteins that make up cells. The information in the DNA molecules must first be transcribed into the complementary sequence of messenger ribonucleic acid (mRNA). The messenger RNA directs the assembly of amino acids into the specific linear sequence characteristic of a particular protein through a process called translation.

Another kind of RNA, called tRNA, carries or transfers individual amino acids from the free state inside the cell to the mRNA in the sequence coded in the mRNA.

The translation process begins when a particular tRNA attaches itself to a particular amino acid in a reaction catalyzed by an enzyme called aminoacyl-tRNA synthetase. Each type of synthetase is specific for one of the 20 different amino acids found in proteins. For example, leucyl-tRNA synthetase selectively binds itself to both the amino acid leucine and to the tRNA for leucine. Similarly, the other tRNA molecules are attached to their corresponding amino acids by their corresponding synthetase.

Each tRNA molecule included three special nucleotide bases, called the anti-codon, which interacts with three complementary codon bases in the messenger RNA. Thus, the tRNA molecule weakly attaches itself at the corresponding location along the mRNA chain. The next codon site along the mRNA chain accepts the corresponding tRNA anti-codon. The amino acid on the first tRNA is cleaved from its tRNA and attaches to the free end of the amino acid on the second tRNA. Sequentially, additional tRNA : amino acid molecules carrying their amino acids attach to subsequent mRNA sites, with the growing chain, cleaving and reattaching to each next tRNA amino acid, each such shift adding one amino acid to the chain.

Eventually, a specific polypeptide chain corresponding to the coding in the original DNA is formed. The above discussion is limited to a discussion of the growth of the chain by translaton, since the method of this invention is involved in only that portion of protein production. Other steps and mechanisms, such as those for starting chain growth, are not relevant to the method of this invention.

The process described above can be adapted to the manufacture of a number of different beneficial polynucleotides, such as those described in my earlier U.S. Pat. Nos. 4,358,586 and 4,401,759. Analogs of medically or commercially important enzymes, hormones, or proteins, more powerful than the corresponding natural ones may be produced in large amounts by cloning and applying my methods listed below they may be commercially or medically important proteins, enzymes, peptide hormones, antibiotics, peptides, peptides modified after cloning helpful in fixation of nitrogen, fermentation adjuncts in specific feedstocks, or the like.

Peptide analogs built to order may be obtained by application of my methods listed in this application (examples of endorphin analogs made in cloning process are listed below), regardless of the sequence of DNA cloned, and regardless of whether the DNA sequence was synthesized e.g. to produce insulin A & B chain, or somatostatin; or the DNA gene was captured by deoxynucleotide as in my endorphin, or any other state of the art method of arriving at DNA that is later cloned. Also, the structure of the original DNA can be modified, or selected anti-codons may be spliced into an mRNA chain to replace or add to the natural anti-codon sequence. The resulting protein will then be modified when the tRNA complementary to the new anti-codon inserts its amino acid at that point into the protein chain being produced.

These prior known methods for producing selected proteins, while useful, have several disadvantages. Solid state techniques are slow and expensive. Cloning, while effective with "natural" proteins such as endorphin, interferon and insulin, has not in the past been capable of producing clones of analog proteins.

Often, it is desirable to produce analogs of beneficial proteins, such as endorphin, with improved properties by replacing certain selected amino acids in the protein chain. For example, analogs of endorphin have been produced by the solid state method that have various combinations of certain desirable properties. The solid state method, unfortunately, is a very slow process of assembling the protein one amino acid at a time. However, the analogs of endorphin so produced have been found to produce greater relief from pain, longer-lasting pain relief, be more lipophilic or lipophobic in certain portions of the molecule and be more resistant to enzymatic degradation (as is the case with D-ala-2-endorphin) when compared with natural endorphin. Also, analogs may be beneficial when patients become refractory to the effects of the natural endorphin.

While such analogs have been produced by solid state methods, those methods have a number of problems.

Solid state methods of "stitching" individual amino acids together in the proper order are severely limited by the many steps and extended time involved in linking one amino acid to the next to form the growing peptide chain and the low yield at each step. Also, isolating the desired peptide free from the many impurities is difficult.

SUMMARY OF THE INVENTION

The above-noted problems, and others, are overcome by a method which basically comprises the steps of selecting an mRNA molecule capable of producing an unmodified protein which has characteristics which are to be improved, selecting an amino acid substitution to be made in the protein chain ordinarily produced by said mRNA through translation, determining the codon along the mRNA chain which ordinarily provides the normal or first amino acid to be replaced by a second amino acid, modifying the tRNA having the anti-codon which would ordinarily complement the codon at that site to ordinarily deliver the first amino acid thereto in a way which will cause it to instead deliver the second amino acid thereto and finally conducting translation of said mRNA in the presence of the modified tRNA and the appropriate tRNA for the other required amino acids, whereby an analog of the protein ordinarily produced by said mRNA results. The modified protein will have the second amino acid in place of the first amino acid.

The required modification of the tRNA can be accomplished in several ways. Either a different amino acid may be substituted for a natural amino acid in a given protein (e.g., alanine-2 for glycine-2 in endorphin) or an amino acid analog may be substituted for the natural amino acid in the protein (e.g., p-chlorophenylalanine for phenylalanine in position 4 of endorphin).

One method of accomplishing the above-described modification of the selected tRNA is misacylation. Here, an x-tRNA(y) is formed where "x" and "y" are amino acids so that "x" is inserted into the protein where the mRNA codon calls for "y". Misacylation is facilitated by dimethylsulfoxide, cacodylate and methanol, as detailed below.

Another method for modifying the selected tRNA is changing the anti-codon of the selected tRNA to the anti-codon of the tRNA carrying another amino acid by chemical means such as the use of bisulfite, as detailed below. Also, one may synthesize tRNA(y) with the anti-codon for the tRNA corresponding to amino acid "x", so that the tRNA will deliver amino acid "y" in place of "x" as the protein is grown through translation.

Where the second amino acid is an analog of the first, and not totally different, the tRNA which ordinarily carries the first amino acid can be modified by "forcing" it to accept and carry the second. Often, this can be accomplished by merely mixing the analog (e.g., p-chlorophenylalanine) into the translation mixture in place of the ordinarily called-for natural amino acid (e.g., phenylalanine). In other cases, it is desirable to load the analog into the corresponding tRNA prior to adding it to the translation solution.

Also, an x-tRNA(x) can be modified to y-tRNA (x) by chemical or enzymatic means such as the conversion of cys-tRNA(cys) to ala-tRNA(cys) by reduction of cystein in the presence of Raney nickel.

One may cleave tRNA into 2 approximately equal halves neither half containing anti-codon; and add one of the 57-60 other anti-codons to one of the tRNA halves. The original half plus the other with its altered anti-codon may now be allowed to snap together.

Incubation of t-RNA CC-OH (lacking terminal A group) with preaminoacylated PIP2 di(adenosine 5prime) diphosphate may be accomplished in the presence of purified RNA ligase transferred an aminoacyladenylate to the 3' terminus of the shortened t-RNA in yields 38-79% also t-RNA CC—OH (2.5 to 4 A260 units) may be incubated with 14 A256 units of aminoacylated diadenosine diphosphate in presence of 10.5-18 units of RNA ligase. After 4-8 hours of incubation, the desired aminoacyl tRNA may be separated from unreacted starting material by chromatography on BD cellulose. Additionally, Use of aminoacyl tRNA containing non-cognate amino acid or analog may be used to insert a non-cognate amino acid or analog into a peptide chain, in place of the normal amino acid.

DETAILED DESCRIPTION OF THE INVENTION

Details of the invention, and of certain preferred embodiments thereof, will be further understood upon reference to the following description of the method of this invention. All parts and percentages are by weight unless otherwise indicated.

In preparing analogs of useful proteins which have improved properties, the first step is selecting analogs for pharmaceutical testing which are likely to be beneficial. Typical systems for investigating the likely pharmaceutical characteristics of a yet to be built protein have been described by P. Gund et. al., Science (1980) 208, 1425 and others. Typical of these is the Crystnet System where typical functions are network access to a protein data base, large molecular display in three dimensions and drug-enzyme docking studies. Similarly the MMS-X System provides conformational analysis, receptor mapping and protein crystal fitting.

Using these known characteristics of proteins and amino acids, one or more substitutions which appear likely to produce improved properties are selected. Typical selections might be certain analogs of "natural" endorphin and enkephalin. The following analogs appear to be favorable: $3,4Cl_2$ phenylalanine 4; D-alanine 2 met 5 enkephalin; D-alanine 2, $3CF_3$ 4CL phenylalanine 4; met 5 enkephalin and their corresponding endorphins.

Sufficient of the selected enkephalin and endorphin analogs are then synthesized by solid state techniques to test their analgesic properties by any conventional test, such as the rat tail flick test, comparing the analog with "natural" endorphin and enkephalin whether administered intravenously, inter-muscularly or by injection into the spinal column. The most promising analog candidates are then produced on a macro scale by the amino acid insertion and cloning methods of this invention, using any suitable combination of my methods as set forth above.

One method for inserting D-amino acids into proteins is as follows. I have found that D-alanin 2 met 5 enkephalin is a much more effective analgesic and has a greater resistance to enzymatic degradation when compared to "natural" met-enkephalin.

Typical conditions for forming D-alanine tRNA (ala) are as follows: A reaction mixture (0.4 ml) is prepared containing about 100 mm 2-mercaptoethamol, about 100 micrograms/ml BSA, about 0.25 mM D-alanine, 2 to 15 A260 units E. coli tRNA and an excess (about 4 units) E. coli tRNA synthetase. Reaction is allowed to proceed for about 10 minutes. The D-alanine tRNA (ala) is isolated by acid precipitation and filtration in the manner described by Calendar and Berg, Biochemistry, 5, 1690 (1966).

The D-alanine is incorporated into the protein in a translation mixture containing the D-alanine tRNA (ala) made above. Cloning then is carried out by any of the techniques described in my above referenced U.S. Patents, with D-ala tRNA(ala) added, and as sole source of alanine in the cloning mixture.

In another amino acid substitution technique, tRNA may be misacylated by non-cognate amino acids in the range of about 1 to 0.1% under the conditions present in in vivo translation. Yields may be increased up to about 70-80% loading by non-cognate amino acids by control of in vitro conditions which include the use of solvents such as dimethylsulfoxide, methanol, cacodylate ion; pH; ratio of synthetase to tRNA; and temperature. Generally, a pH of about 8.25 to 8.75 is optimum for misacylation. Optimum results are also obtained with temperatures in the 30-37 degree C. range. There is almost a linear increase in misacylation as dimethylsulfoxide or ethanol is increased to about 20%, while over 20% misacylation decreases.

The length of the protein chain is controlled by the insertion of a stop signal. The mRNA's that contain codons UGA, UAA, and UAG will translate all codons into corresponding amino acids stitched into the protein chain up to but not including the codon for termination; no further amino acids will be added thereafter. For insertion of stop codons UGA, UAA, and UAG, the corresponding deoxynucleotides must be inserted at the appropriate places into the DNA to be cloned. For example, if met enkephalin is to be produced in a clone terminating in methionine 5, the following deoxynucleotides are typical of those which may be used:
d-TCA CAT GAA CCC CCC GTA
d-TTA CAT GAA CCC CCC GTA
d-CTA CAT GAA CCC CCC GTA If beta-endorphin is to be produced from a clone the termination signals need to be inserted terminating endorphin at gln 31. Deoxynucleotide probes which accomplish that purpose have the general formula:
d-TCA xTG zCC xTT xTT yTG
d-TTA xTG zCC xTT xTT yTG
d-CTA xTG zCC xTT xTT yTG
wherein "x" is C or T, "y" G or A and "z" is A, G, C or T.

Any suitable amino acid may be inserted into a protein in place of another amino acid to modify the properties of the protein. Typical amino acids which may be used include the 20 basic amino acids and p-aminophenylalanine, p-fluoro, m-fluoro, o-fluoro phenylalanine, ethionine, norleucine, seleno-methionine, aza-tryptphane, 2-thienyl alanine, azetidine 2 carboxylic acid 1, 2, 4 triazolealanine, beta hydroxy aspartic acid lanthionine, citrulline, sarcosine, 3, 5 di-iodo tyrosine, and alpha amino isobutyric acid.

Another method for synthesizing analogs by use of the techniques of my invention will be described for several selected enkephalins and endorphins which I have found to have superior properties. These analogs are D-ala2-4-chlorophenylalanine-4-met enkephalin; D-ala2-3CF3, 4Cl phenylalnine-4 met enkephalin; D-ala2-3, 4(CF3)2 phenylalanine-4 met enkephalin; and D-ala2-3CF3, 4-NO2 phenylalanine-4-met enkephalin and their corresponding beta endorphins.

The synthesis of these analogs is based on cloned material from beef endorphin gene. There are basically four steps involved in obtaining each of the above-listed analogs. First, the codon gly 2 is changed to ala 2. Next the peptide is terminated at the end of the fifth amino acid (met enkephalin) or thirty-first amino acid (for beta endorphin). Next d-ala 2 is inserted in place of gly 2. The first two tasks will be perfomed by the use of one probe to produce enkephalin and two probes to produce endorphin (one probe to substitute alanine for glycene 2 and the other probe to terminate the peptide chain). These probes are used in the manner described in my two copending U.S. Patent applications listed above. The probes for enkephalin are TTA CAT yAA zCC zGC yTA; TCA CAT yAA zCC zGC yTA; and CTA CAT yAA zCC zGC yTA with the endorphin probes being any of these plus TTA xTG zCC xTT xTT yTG; TCA xTG zCC xTT yTA; CTA xTG zCC xTT xTT yTG; wherein "x" is C or T, "y" G or A, and "z" is A, G, C or T and the underlined triplet is the "stop" signal, with (in the first set of sequences) the underlined single nucleotide identifying the substitution of alanine 2 for glycene 2. The third step is accomplished by preparing D-ala tRNA (ala) as described above. Similarly, the fourth step is accomplished by substituting the desired phenylalanine analog into the phe tRNA·(phe) in the cloning mixture, omitting all phenylalanine therefrom.

The following examples provide a specific preferred embodiment of the method of my invention within the context of the more general method described in detail above. These examples detail a preferred method of analog production, together with preferred tests to assure that the selected analog is actually produced. All parts and percentages are by weight unless otherwise indicated.

EXAMPLE I

Extraction of m-RNA (endorphin) is performed by the following method. Beef pituitary is removed from fresh beef carcasses at the abattoir. The pituitary is finely minced and mixed with about 0.1 m. per g. of Dulbecco's medium (available from Gibco, Catalog No. 320). The mixture is pureed in a Waring blender. To the puree is added about 0.8 m./g. Dulbecco's medium, about 0.1 mg/g fetal calf serum, about 0.5% proteinase K, about 1 microliter per gram tissue of a radioactive amino acid (as a tracer) and about 0.5% collagen. The mixture is incubated for about 30 minutes at about 37° C. Then sufficient cycloheximide is added to produce an about 1 microM concentration and the mixture is incubated for about two minutes. Solid cell matter is filtered out using several layers of cheesecloth. Cells from the filtrate are pelleted by centrifuging for about ten minutes at about 1000 G. The cells are washed with a mixture of RSB (a rinse buffer containing about 10 mM Tris (hydroxymethyl amino methene sulfonic acid), pH 7.4, about 10 mM NaCl, about 3 mM $MgCl_2$) and about 1 mM cycloheximide. The cells are then resuspended in RSB, then are lysed with 1/10 vol. Nonidet P40 (a non-ionic detergent available from Sigma) and are allowed to settle for about five minutes with gentle agitation. The mixture is then centrifuged for about five minutes at about 900 G. and the supernatant is collected. The supernatant is treated with an equal volume of 5% Triton X-100 (an ionic detergent from Sigma) and agitated for about five minutes. The pH is lowered to about 5.3 with 2m HCl. The mixture is then centrifuged for about five minutes about 8000 G. The pellets produced are crude polysomes. The polysomes are resuspended in a minimum volume of a Borate Buffer (about 0.1 M borate, pH 8.2, and 1% BSA, bovine serum albumin). Next the m-RNA (endorphin) present in the polysome suspension is isolated by antibody purification. A small affinity column of Sepharose 4B (an exclusion chromatography resin, Pharacia 17-0120-01) is washed with anti-ACTH (an antibody that binds selectively to adrenocriticotrophic hormone) with about 0.1 M Hac (acetic acid) at about 4° C. The column is prepared with about 5 volumes Borate Buffer. The polysome suspension sample is then added to the affinity column which is allowed to equilibrate overnight. Unreacted mRNA is then washed out with Borate Buffer. The column is then washed with 1 volume saline Triton Buffer (1%BSA, 0.1 M borate (pH 8.2), 0.2% Triton X-100 and 0.3 M NaCl), then with 0.1 volume of a 10/1 dilution Borate Buffer, then with 1 volume 0.1 M HAc. This is the main elution; a check of the radioactive count will show the relative amount of enriched mRNA (endorphin) present. The column is then washed with about 1 volume of 0.001 M HCl, and finally with about 1 volume of 0.12 M HCl.

EXAMPLE II

Glutamine t-RNA (glu) is prepared and purified as follows. One unit (50 micrograms) t-RNA (glu), about 5 microliters *glutamine (6.25 nM), one unit synthetase (an enzyme which transfers amino acid to its corresponding t-RNA), about 100 micrograms BSA, about 2 mM ATP (adenosine triphosphate), about 70 nM $MgCl_2$ and about 10 mM beta-mercaptoethanol are mixed together, then the mixture is maintained at about 35° C. For about two hours. About 100 microliters of this crude glutamine t-RNA (glu) mixture is mixed with about 660 microliters TCA (tri-chloroacetic acid), a Sephadex G-200 buffer to make 1 volume, 1% KAc (potassium acetate), pH 4.6, and a small amount of the marker, Blue Dextrose. The mixture is applied to a Sephadex G-200 column (an exchange chromatographic resin, Pharmacia 17-oo81-01). The glutamine t-RNA (glu) appears as a discrete peak where maxima are obtained for radioactivity due to glutamine and color for t-RNA, thus confirming that they are combined.

EXAMPLE III

The following method translates m-RNA (endorphin) to produce an endorphin analog in which phe 4,18 is replaced by $pNH_2$ phe 4,18. A translation mixture is prepared consisting of: 35g. total polysomal RNA enriched in m-RNA (endorphin), (obtained in Example I) 100 lambda reticulocyte lysate mixture; 30 lambda 10X aminoacid mixture minus gly, tyr, phe; $PNh_2$ phe in 30 lambda 100 X 25 lambda 60 mM fructose diphosphate; 60 lambda placental ribonuclease inhibitor (300 u.); 85 lambda KAc (2M); 150 lambda *tyr (1mCi/1 ml.); and 100 lambda *gly (1 mCi/1 ml.). This mixture is mixed gently and allowed to incubate at about 30° C. for about 90 minutes. The reaction is stopped by placing the reaction vessel on an ice bath. About ten microliter samples are placed on Ecteola paper strips which are then washed with KAc and HAc. The resulting product on the strips at this point is ACTH/Beta liptropin.

EXAMPLE IV

Free endorphin analogs are produced by cleaving ACTH/Beta liptropin with clostripain according to the following method. Clostripain cleaves preferentially only at arginine sites. I have found that this applies to the endorphin precursors described above. Therefore, lysine groups need not be protected by citraconic anhydride or the like. A sample of the protein products produced in Example III is heated on a steam bath for about five minutes. About 6 sample volumes of a sample buffer consisting of about 0.1 M $NaPO_4$ (pH 7.8) and about 0.005 M DTT (dithioerythreitol), is mixed with the sample and about 1/10 sample vol. of clostripain (12.38 mg/ml) is added thereto. The mixture is heated on a steam bath for about five hours at about 30° C. The remains are then solubilized in a buffer mixture of about 0.15 M pyridine and pH is adjusted to about 3.04 with HAc. Cleavage products are then fractionated on a Sephadex G-75 (an exchange chromatographic resin, Pharmacia 17-0051-01) column as previously described. A pronounced peak of radioactive peptide is obtained corresponding to the molecular weight of endorphin (M 3500).

EXAMPLE V

That the structure obtained is that of the desired analog is proved by the following method. The first 8 amino acids are removed in order by Edman Degradation. Phenylisothiocyanate (PITC, the Edman reagent) reacts with the polypeptide to yield a phenylthiohydontain (PTH-) derivative of the N-terminal acid that can be identified chromatographically. The resulting polypeptide (minus the N-terminal amino acid) is treated again by the same procedure to identify the next amino acid. Each amino acid thus removed is placed separately on thin layer chromatographic material. Control chromatographs are run with known samples of the amino acids which should be present if my product structure is correct. The positions of the samples produced above result in chromatographs identical with the control samples, confirming that the endorphin analog having $pNH_2$ phe 4,18 in place of the phe 4,18 is produced.

EXAMPLE VI

The following method translates m-RNA (endorphin) to produce an analog in which glu 8 is replaced by gln 8. A translation mixture is prepared consisting of about 35 micrograms of total polysomal RNA enriched in m-RNA (endorphin) prepared as detailed in Example I; 100 lambda reticulocyte lysate mixture; 30 lambda 10x amino acid mixture minus gly, tyr and glu; a 10-fold molar excess over average amino acid (100x) of gln t-RNA (glu) prepared as in Example II, 25 lambda 60nM fructose diphosphate, 60 lambda placental ribonuclease inhibiter (300 u); 85 lambda KAc (2M); 150 lambda *tyr (lmCi/ml); 100 lambda *gly (lmCi/ml). This mixture is mixed gently and allowed to incubate at about 30° C. for about 90 minutes. The reaction is stopped by placing the reaction vessel on an ice bath. About 10 microliter samples are placed on ECTEOLA paper strips which are then washed with KAc and HAc. The resulting product on the strips at this point is ACTH/Beta lipotropin. The ACTH/Beta is then cleaved by clostripain as described in Example IV. A pronounced radioactive peptide peak is obtained corresponding to the molecular weight of endorphin. The structure obtained is confirmed by the method described in Example V to be the endorphin analog having glu 8 in place of gln 8.

EXAMPLE VII

The steps of Examples I-V are further repeated to produce other analogs of endorphin as follows:
(a) to provide pCl phe in place of phe;
(b) to provide thiolysine in place of lys;
(c) to provide $pNO_2$ in place of phe 8; and
(d) to provide ala2 in place of gly 2.

In each case, the test of Example V shows that the desired analog is produced.

While the above description of the method of my invention and of several preferred embodiments thereof described certain specific analogs, amino acid substitutions, temperatures, etc., these may be varied, where suitable with similar results.

Other variations, applications and ramifications of my invention will become apparent to those skilled in the art upon reading this disclosure. These are intended to come within the scope of this invention as defined in the appended claims.

I claim:

1. The method of inserting amino acid analogs into proteins to produce modified proteins, which comprises the steps of:
   providing an mRNA molecule capable of producing an unmodified protein through translation;
   selecting a codon along the mRNA which would ordinarily accept during translation a corresponding anti-codon of a tRNA carrying a first amino acid;
   modifying said tRNA so that it carries a second amino acid; and
   conducting translation of said mRNA in the presence of said modified tRNA and tRNA from other required amino acids whereby an analog of the protein ordinarily produced by said mRNA results with said second amino acid in the protein chain in the position ordinarily occupied by said first amino acid.

2. The method according to claim 1 wherein said tRNA is modified by replacing the amino acid ordinarily carried thereby with a second amino acid through misacylation.

3. The method according to claim 1 wherein said tRNA is modified by changing the anti-codon for a tRNA carrying the second amino acid so as to be complementary to a codon ordinarily accepting only a tRNA carrying a first amino acid.

4. The method according to claim 1 where the tRNA for said second amino acid is synthesized with the anti-codon for the first amino acid so that the anti-codon will carry said second amino acid to the site ordinarily accepting the first amino acid, and increasing the amount to said modified tRNA through cloning.

5. The method according to claim 1 wherein said second amino acid is an analog of said first amino acid and the tRNA which ordinarily carries the first amino acid is loaded only with the second amino acid.

6. The method of inserting amino acid analogs into proteins to produce modified proteins which comprises the steps of:
   providing fresh beef pituitary;
   extracting m-RNA (endorphin) therefrom;
   preparing glutamine t-RNA (glu);
   preparing a translation mixture comprising reticulocyte mixture, an amino acid mixture minus selected amino acids, fructose diphosphate, placental ribonuclease inhibitor, potassium acetate, *typ and *gly;
   incubating said translation mixture;
   adding to a sample of said translation mixture sodium phosphate, dithioerythreitol and clostripain;
   heating said sample for a suitable period;
   solubilizing the remains; and
   fractionating the product to isolate the endorphin analog produced.

7. The method of producing an analog of endorphin having $pNH_2$ phe 4,18 in place of phe 4,18 which comprises the steps of:
   removing beef pituitary from fresh beef carcasses;
   preparing a puree of said beef pituitary with about 0.1 ml/g Dulbecco's medium;
   mixing therewith about 0.8 ml/g Dulbecco's medium, about 0.1 mg/g fetal calf serum, about 0.5% proteinose K, about 0.5% collagen;
   incubating the resulting mixture for about 30 minutes at about 37° C.;
   adding thereto sufficient cycloheximide to produce an about 1 microM concentration;
   incubating the resulting mixture for about 2 minutes;
   filtering out any solid material;
   pelleting cells from the filtrate;
   washing the pelleted cells with a mixture of RSB, about 10 mM sodium chloride, about 3mM magnesium chloride and about 1mM cycloheximide;
   resuspending the cells in RSB;
   lysing said cells with 1/10 volume nonoionic detergent;
   centrifuging the resulting mixture at about 900 G for about 5 minutes;
   treating the supernatant with an equal volume of an ionic detergent solution (5%) with agitation for about 5 minutes;
   reducing the mixture pH to about 5.3%;
   centrifuging the mixture for about 5 minutes at about 8000 G to produce crude polysome pellets enriched in m-RNA (endorphin);
   resuspending said polysomes in a minimum volume of a mixture comprising about 0.1 M borate, about 1% bovine serum albumin;
   isolating the m-RNA (endorphin) present in the polysome suspension by antibody purification in an affinity column;
   preparing glutamine t-RNA (glu), about 5 microliters * glutamine, about one unit synthetase, about 100 micrograms bovine serum albumin, about 2mM adenosine triphosphate, about 70 nM magnesium chloride and about 10 mM beta-mercaptoethanol and maintaining the mixture at about 35° C. for about 2 hours to produce crude glutamine t-RNA (glu);
   mixing about 100 microliters of this crude mixture with a mixture comprising about 660 microliters tri-chloroacetic acid, a buffer to make 1 volume, and about 1% potassium acetate;
   isolating glutamine t-RNA (glu) on a chromatographic exchange column;
   translating m-RNA (endorphin) to produce the endorphin analog as follows:
      preparing a translation mixture in a reaction vessel comprising about 35g. of said resuspended polysomes; about 100 lambda reticulocyte lysate mixture; about 30 lambda 10x aminoacid mixture minus gly, tyr, phe; about 100x said glutamine t-RNA (glu); about 25 lambda 60 mM fructose diphosphate, about 60 lambda placental ribonuclease inhibiter (300 u.); about 85 lambda KAc (2M); about 150 lambda *tyr (1mCi/ml.); and about 100 lambda *gly (1mCi/ml.);
   incubating the mixture at about 30° C. for about 90 minutes;
   placing the reaction vessel on an ice bath to stop the reaction;
   whereby ACTH/liptropin is produced;
   cleaving said ACTH/liptropin to produce free endorphin by:
   heating said ACTH/liptropin on a steam bath for about 5 minutes;
   mixing one sample volume of said ACTH/liphtropin with about 6 sample volumes of a sample buffer and about 0.1 sample volume of 12.38 mg/ml clostripain;
   heating the resulting mixture for about 5 hours at about 30° C.;
   solubilizing the resulting remains in a pyridine buffer; and
   fractionating the resulting cleavage products;
   whereby an endorphin analog fraction having $pNH_2$ phe in place of phe 4,18 results.

* * * * *